US006655192B2

United States Patent
Chavdar

(10) Patent No.: US 6,655,192 B2
(45) Date of Patent: Dec. 2, 2003

(54) PERMEAMETER-POROSIMETER

(75) Inventor: Bulent Chavdar, Wheaton, IL (US)

(73) Assignee: BorgWarner Inc., Troy, MI (US)

( * ) Notice: Subject to any disclaimer, the term of this patent is extended or adjusted under 35 U.S.C. 154(b) by 111 days.

(21) Appl. No.: 09/974,179

(22) Filed: Oct. 10, 2001

(65) Prior Publication Data

US 2003/0066339 A1 Apr. 10, 2003

(51) Int. Cl.$^7$ .............................................. G01N 15/08
(52) U.S. Cl. .............................................. 73/38; 73/37
(58) Field of Search ...................................... 73/37, 38

(56) References Cited

U.S. PATENT DOCUMENTS

| | | | |
|---|---|---|---|
| 3,577,767 A | 5/1971 | Stedile | 73/38 |
| 3,882,714 A | 5/1975 | Libal et al. | 73/38 |
| 3,939,698 A | 2/1976 | De Lacy | 73/73 |
| 4,203,317 A | 5/1980 | Gupta | 73/38 |
| 4,300,386 A | 11/1981 | Gupta | 73/38 |
| 4,453,398 A | 6/1984 | Demirel et al. | 73/38 |
| 4,517,825 A | 5/1985 | Grollimund et al. | 73/38 |
| 4,524,605 A | 6/1985 | Italiano et al. | 73/38 |
| 4,531,404 A * | 7/1985 | Phelps et al. | 73/38 |
| 4,561,289 A * | 12/1985 | Jones | 73/38 |
| 4,643,019 A * | 2/1987 | Jones | 73/38 |
| 4,679,422 A * | 7/1987 | Rubin et al. | 73/38 |
| 4,718,270 A | 1/1988 | Storr | 73/38 |
| 4,753,107 A * | 6/1988 | Reed et al. | 73/38 |
| 5,050,493 A * | 9/1991 | Prizio et al. | 100/106 |
| 5,065,421 A * | 11/1991 | Morineau et al. | 378/208 |
| 5,394,737 A * | 3/1995 | Prange et al. | 73/38 |
| 5,736,632 A * | 4/1998 | Nishida et al. | 73/38 |
| 5,832,409 A * | 11/1998 | Ramakrishnan et al. | 702/12 |
| 5,844,136 A * | 12/1998 | Marsala et al. | 73/38 |
| 5,979,223 A * | 11/1999 | Fleury | 73/38 |
| 5,983,708 A * | 11/1999 | Mayer et al. | 73/38 |
| 6,021,661 A * | 2/2000 | Lowell et al. | 73/38 |
| 6,055,850 A * | 5/2000 | Turner et al. | 73/38 |
| 6,094,967 A | 8/2000 | Cavdar | 73/9 |
| 6,178,808 B1 * | 1/2001 | Wang et al. | 73/38 |
| 6,298,711 B1 * | 10/2001 | Volfkovich et al. | 73/38 |
| 6,401,523 B1 * | 6/2002 | Fernandes et al. | 73/38 |

OTHER PUBLICATIONS

European Search Report; EP 02 25 6704; Feb. 7, 2003.
Abstract/Zusammenfassung/Abrege 02256704.4.
Bulent Chavdar, A Permeameter Measuring Normal and Lateral Permeability And An Investigation On Wet Friction Materials; May 12 –16, 2002; 47$^{th}$ International SAMPE Symposium; XP–001145423.
Not Just Products . . . Solutions PMI Und App; XP–000825742.

* cited by examiner

Primary Examiner—Hezron Williams
Assistant Examiner—David J. Wiggins
(74) Attorney, Agent, or Firm—Emch, Schaffer, Schaub & Porcello Co., L.P.A.

(57) ABSTRACT

A permeameter provides normal and lateral permeability measurements on porous materials. The permeability measurements can be made on compressed or uncompressed samples and can be made at room temperature or at elevated temperatures. A wide variety of fluids, gas or liquid, can be used as the penetrating test fluid depending on the application and the porosity of porous sample. The penetrating test fluid is forced through the sample under pressure. The load, the fluid displacement, and the time are recorded and used in the calculations of permeability, porosity, pore size distribution, average pore size and the number of pores per unit area.

21 Claims, 8 Drawing Sheets

PERMEAMETER-POROSIMETER

BACKGROUND OF THE INVENTION

The present invention is directed to a new permeameter-porosimeter (hereinafter referred to as "permeameter") to measure the permeability and porosity of porous materials in normal and lateral (i.e. perpendicular to the normal) directions. The permeability of woven or non-woven, sheet or plate porous materials such as paper, cloth, plastic foam, fritted glass, metal-wool, powder metal, etc. can be measured with the new permeameter. The permeameter of the present invention is well suited for measuring the permeability of friction materials for wet clutch applications; however, it can be applied to any porous material which has three-dimensional structural integrity. The new permeameter is capable of compressing a sample mechanically and taking permeability measurements on the compressed sample. The permeameter also allows measurements at elevated temperatures up to 150° C. The permeameter measures permeability, porosity, pore size distribution, average pore size and number of pores per unit area.

The importance of permeability on the performance of friction materials has been demonstrated in the mathematical models of clutch engagement. However, there is little experimental information on the permeability of friction materials partly due to the absence of a permeameter which can take accurate measurements in normal as well as lateral directions.

The permeability of friction material has a significant impact on torque response as the permeability affects the initial coefficient of friction.

In the past, an oil absorption test has been used as an indirect measure of the permeability and porosity of friction materials. However, the oil absorption test has certain shortcomings which are overcome by the permeameter of the present invention.

SUMMARY OF THE PRESENT INVENTION

The permeameter of the present invention includes three units: 1) sample compartment with compression capability; 2) fluid chamber containing permeant and having a pressurizing piston and a temperature control; and, 3) fluid storage tanks and closed loop transport lines to fill the fluid chamber. Permeant fluid can be gas or liquid depending on the test method. The permeant fluid is forced through the sample under pressure. Measurements of load, fluid displacement, flow time, sample thickness and sample weight before and after the test are recorded and used in the calculations of permeability, porosity, pore size distribution, average pore size and number of pores per unit area.

Normal permeability and lateral permeability are measured separately. The normal permeability measurement requires a disk shaped sample and the lateral permeability measurement requires a ring shaped sample. Both samples can be punched out in a single die cut operation where the disk sample is the center slug of the ring sample. In the normal permeability test, the penetrating fluid is forced through the disk sample along the thickness from one flat side to the other. In the lateral permeability test, the fluid is forced through the ring sample along the annulus from inner diameter to the outer diameter.

Sometimes it is necessary to measure the permeability of materials (especially of the highly compressible ones) when they are under compression. Compression changes the shape and the size of the pores, thereby effecting the permeability. For example, a paper based gasket material functions under a compression to prevent oil leakage. It is important to know the optimum compression needed for an effective sealing since under-compression causes leakage and over-compression reduces the life of gasket. The permeameter of the present invention has the ability to mechanically compress the sample and take permeability measurements on the compressed sample.

A commercially available universal test machine with calibrated force and displacement controls my be used to actuate the piston of the permeameter. The permeameter of the present invention may be used to measure the lateral permeability of a wide range of finished friction plates up to 190 mm diameter.

THEORETICAL BACKGROUND

A Reynolds number check indicates that the flow is laminar during a liquid permeability test. Hence, Darcy's formula is applicable to calculate the permeability constant. Furthermore, it is also assumed that all the pores are cylindrical and of same size. In reality, the pores have random shape and size. However, the uniform pore assumption lets us to calculate an equivalent mean pore diameter, and an equivalent number of pores for the tested samples.

The normal permeability is calculated using the following formula:

$$k_z = \frac{Q \eta l}{\Delta P A} \qquad (1)$$

$k_z$ is the normal permeability (m$^2$)
Q is flow rate (m$^3$/s)
$\eta$ is the absolute viscosity of the fluid (Ns/m$^2$)
l is the distance fluid flow through the sample (m)
$\Delta P$ is the pressure difference between fluid inlet and outlet (Pa)
A is the sample area through which fluid flows (m$^2$)

The lateral permeability is calculated using the following formula:

$$k_r = \frac{Q \eta \ln\left(\frac{r_o}{r_i}\right)}{2 \pi t \Delta P} \qquad (2)$$

where $k_r$ is the lateral permeability, $r_o$ and $r_i$ outer and inner diameter of ring sample, and t is the thickness of sample.

The ratio of the volume of the liquid permeant absorbed by the sample to the geometric volume of the sample gives the percent porosity. The percent porosity is calculated from the weight difference of the sample before and after the permeability test using the following formula:

$$\phi_p = \frac{W_A - W_B}{\rho V} 100 \qquad (3)$$

where $\phi_p$ is the percent porosity, $W_A$ and $W_B$ are the sample weight after and before the test, $\rho$ is the density of the fluid, V is the geometric volume of the sample.

The average pore size is determined assuming that the pores are cylindrical, straight, and of equal diameter. Flow through a capillary pore of diameter $d_p$ and length l is given by the following formula:

$$q = \frac{\pi d_p^4 \Delta P}{128 \eta l} \quad (4)$$

Total flow through the sample (Q) is found by multiplying the flow through one pore (q) by the number of pores (N):

$$Q = Nq \quad (5)$$

The total number of pores (N) is obtained by dividing the total pore volume ($V_p$) to a single pore volume ($v_p$):

$$N = \frac{V_p}{v_p} \quad (6)$$

The total pore volume ($V_p$) is found by multiplying the volume of the sample (V) with the percent porosity ($\phi_p$)

$$V_p = V \frac{\phi_p}{100} \quad (7)$$

The individual pore volume is $$v_p = \frac{\pi d_p^2 l}{4} \quad (8)$$

Where ($d_p$) is the pore diameter and (l) is the pore length. In normal permeability, l is equal to the thickness of the disk sample. In lateral permeability, l is equal to the width of the annulus of the ring sample. The mean pore diameter ($d_p$) is calculated by replacing equations 4, 6, 7, and 8 in 5 and extracting $d_p$ $$d_p = \left( \frac{3200 l^2 Q \eta}{\Delta P V \phi_p} \right)^{1/2} \quad (9)$$

The number of pores per unit sample area ($N_{per\ mm^2}$) is given in terms of porosity ($\phi_p$) and mean pore diameter ($d_p$) as follows:

$$N_{per\ mm^2} = \frac{\phi_p}{25 \pi d_p^2} \quad (10)$$

where $d_p$ is in mm.

Pore size distribution is obtained using air as the permeant. The flow rate of air is measured under a ramping air pressure on a dry sample. The dry sample is removed from the permeameter and saturated with a low surface tension wicking fluid until the sample is completely wet. Then, the air flow rate measurement is repeated on the wet sample under the ramping pressure. The flow rate difference between the dry sample and the wet sample at each pressure interval yields information on the pore size distribution.

Fluids of different viscosities can be used in the measurements in order to have enough retention time for accurate measurements. For example, while oil is used for the normal permeability, water can be used for the lateral permeability measurement. Permeability and porosity calculations require the measurements of flow rate and volume of retained fluid, respectively. Permeability (k) and porosity ($\phi$) are independent parameters since the flow rate and the retained fluid volume are measured independently. On the other hand, pore size (d) and number of pores (N) are coupled parameters and not independent from permeability and porosity.

IN THE DRAWINGS

DETAILED DESCRIPTION OF THE INVENTION

Figure 1:
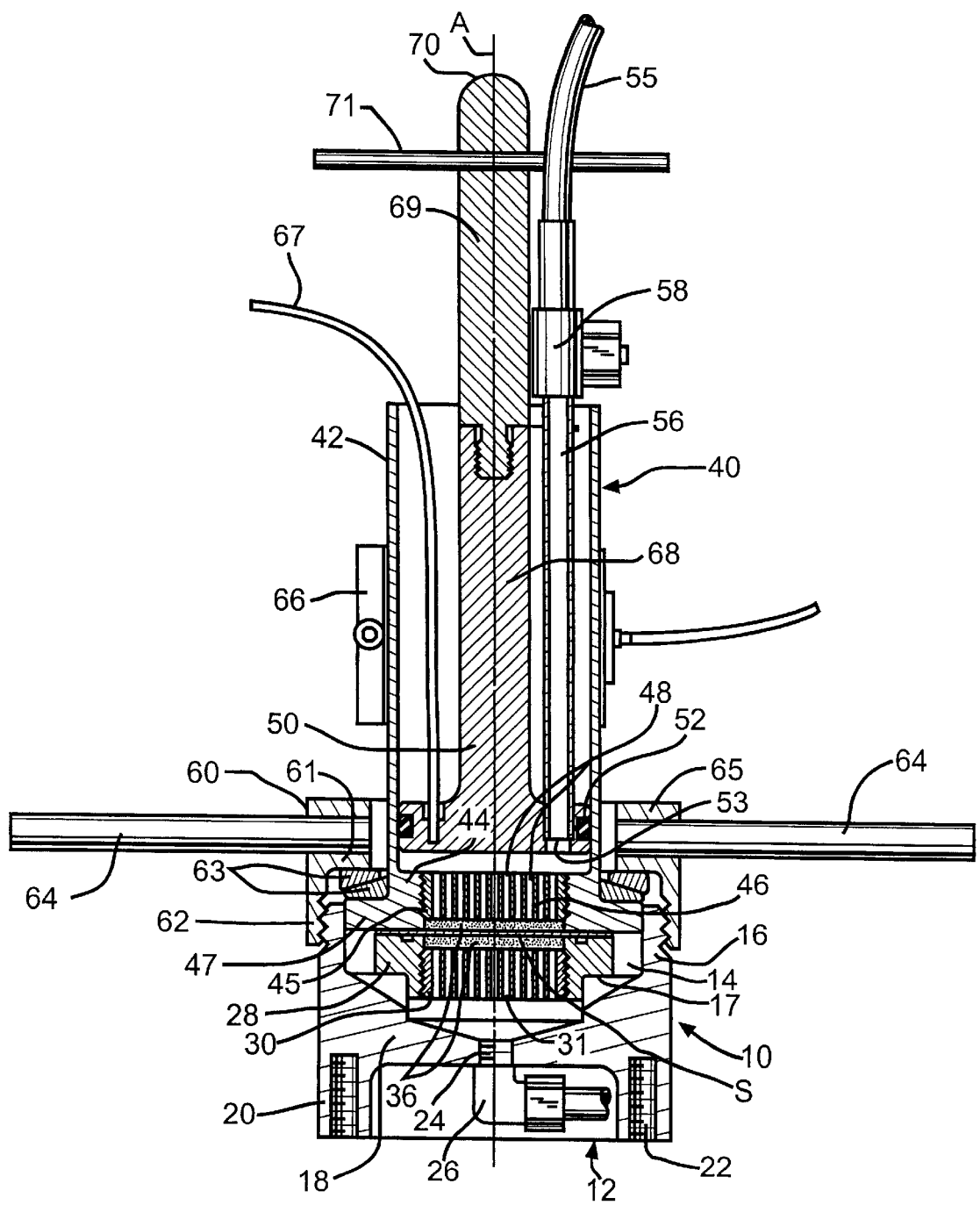
FIG. 1 is a sectional view of one embodiment of the permeameter-porosimeter assembly of the present invention showing testing of a disk-shaped sample in the normal direction.
Figure 2:
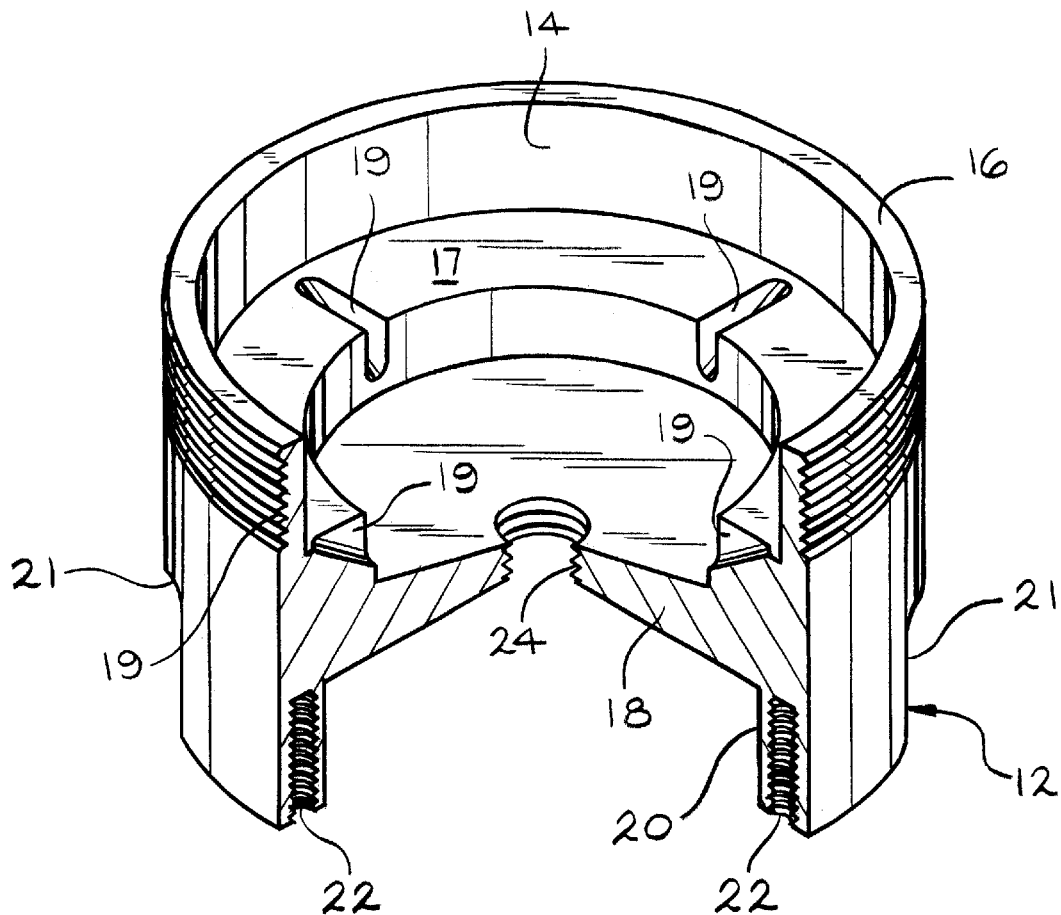
FIG. 2 is a perspective view of the base member of the assembly of FIG. 1.

Referring to FIGS. 1–4 and 9, there is shown a first embodiment of the permeameter-porosimeter assembly of the present invention generally designed by the numeral 10. The assembly 10 extends along an axis A and includes a base 12, a fluid chamber housing 40 and a compression ring 60. The base 12 has a recess 14 facing upwardly and defined by a cylindrical upper sidewall 16 and a transverse wall 18. The cylindrical upper sidewall 16 has external threads 19. Extended downwardly from the transverse wall 18 is a lower cylindrical wall 20 having four radially extending mouse holes 21 spaced 90° from one another and four upwardly extending threaded recesses 22, each spaced 45° from adjacent mouse holes 21 and extending upwardly from the lower edge of the lower cylindrical wall 20. The recesses 22 may have engaged thereto fasteners from a support on which the lower cylindrical wall 20 rests. The transverse wall 18 includes a shoulder 17 extending radially inwardly from the cylindrical upper sidewall 16 and a plurality of slots 19, preferably four in number, positioned 90° from one another.

The transverse wall 18 also has a threaded opening 24 centrally positioned on axis A through which permeant fluid entering the recess 14 may drain. An outlet tube 26 and related connectors receive fluid flowing out of the recess 14 and direct it to fluid storage tanks 11.

Positioned in the recess 14 and resting on the shoulder 17 is a ring-shaped support block 28 having an internal thread 29. The support block 28 has a radially outwardly extending shoulder 27 which rests upon the shoulder 17 of the base 12 and an upwardly facing annular groove 35 in which may be positioned an annular seal.

The support block 28 houses a lower holley block 30 which is threadedly engaged to the internal thread 29. The lower holley block 30 is adjustable on the support block 28 by rotation when in threaded engagement with the support block 28 in order to position its upper end at the desired elevation. The lower holley block 30 is provided with a plurality of flow passages 31 extending axially therethrough. The number of flow passages 31 extending through the lower holley block 30 is such as to occupy substantially the entire transverse area of the lower holley block 30 giving an appearance of a honeycomb when viewed from an axial direction. The number of flow passages 31 coupled with the sizes thereof is such as to have minimal effect on the flow of the permeant fluid flowing therethrough in relation to fluid flowing through a sample being tested. For example, a holley block having an outer diameter of 50.8 mm may have more than 100 flow passages each having a diameter of 3.2 mm.

Engaged to the base 12 is a fluid chamber housing 40 having an upper axially extending tubular section 42 and an enlarged lower section 44. The lower section 44 has a radially outwardly extending flange 47 sized to fit within the cylindrical upper sidewall 16 of the base 12 in close engagement therewith. The lower section 44 is ring-shaped and has internal threads 45 to which may be threadedly engaged an upper holley block 46. The upper holley block 46 has a series of axially extending flow passages 48 similar to the flow passages 31 of the lower holley block 30.

A disk-shaped sample S which is to be tested in the normal direction is positioned between the lower support block 28 and the lower surface of the radial flange 47 of the fluid chamber housing 40 with its outer periphery clamped therebetween, between (i) the upper surface of the support block 28 and, when used, an annular seal positioned in the annular groove 35 and (ii) the lower surface of the radial flange 47. As will be described in detail hereinafter with reference to FIGS. 5 and 6, if the sample is to be tested radially, the sample will be a ring-shaped element, a flat plate 32 will be used and the sample will be positioned between the flat plate 32 and the lower surface of the fluid chamber housing 40 and its radial flange 47.

As shown in FIG. 1, a pair of porous spacers 36 are provided, one positioned in the lower support block 28, engaged to the upper surface of the lower holley block 30, and the other positioned in the opening of the lower section 44 of the fluid chamber housing 40 engaged to the lower surface of the upper holley block 46. The porous spacers 36 may be formed from a foam plastic or a fritted glass and should have a mean pore size at least ten times larger than that of the test sample S so that the effect of the porous spacers 36 on the flow of the permeant will be minimal in relation to the fluid flowing through the test sample.

At the juncture of the upper tubular section 42 of the fluid chamber housing 40 with the lower section 44 there is provided a shoulder extending radially inwardly to the area of the internal threads 45.

Positioned within the upper tubular section 42 is a piston 50 which is axially moveable within the upper tubular section 42. An O-ring 52 provides a seal between the enlarged head of the piston 50 and the interior surface of the upper tubular section 42.

The enlarged head of the piston 50 is provided with an aperture 53 for introducing fluid into the space between the lower surface of the enlarged head of the piston 50 and the lower section 44 of the fluid chamber housing 40. Permeant fluid used for testing is directed from a supply source such as storage tank 11 through tubing 55 to a pipe 56 connected to the aperture 53. A ball valve 58 between the tubing 55 and the pipe 56 controls the flow of the permeant used for testing. The storage tank 11 is placed at a higher level than the fluid chamber housing 40 so that fluid flows by gravity when the ball valves 58 are opened. As may be seen in FIG. 9, a second length of tubing 57 is also connected between the storage tank 11 and the fluid chamber housing 40. The use of two separate lengths of tubing 55 and 57 and ball valves permits one of function as an outlet tube for return of unused portion of the permeant fluid to the storage tank 11 and to prevent air pockets from developing upon introduction of permeant into the fluid chamber housing 40. The storage tank 11 can also be equipped with a hydraulic pump in order to fill the fluid chamber housing 40 more quickly.

The fluid chamber housing 40 is connected to the base 12 by a compression ring 60 having an annular shoulder 61 and an internally threaded skirt 62 engaged to external threads 19 at the upper end of the base 12. A pair of spherical washers 63 are positioned between the shoulder 61 of the compression ring 60 and the upper surface of the radial flange 47 of the fluid chamber housing 40. A pair of torque arms 64 are engaged to ears 65 of the compression ring 60 to assist in threadedly engaging the compression ring 60 to the base 12 at the desired pressure to clamp the lower section 44 of the fluid chamber housing 40 to the peripheral edge of the disk-shaped sample S being tested. The spherical washers 63 are self-aligning under compression and provide a uniform pressure over the test sample S as the compression ring 60 is rotated to the desired pressure by means of a torque wrench and torquing arms 64.

A heater 66 encircles the upper tubular section 42. The heater 66 along with a thermocouple 67 engaged to the enlarged head of the piston 50, function to bring and maintain the testing fluid to the desired temperature for the specific samples being tested.

The piston 50 has a lower shaft 68 extending from the enlarged head and an upper shaft extension 69 threadedly engaged thereto. The upper shaft extension 69 has a spherical top 70. A handle 71 may be engaged to the upper shaft extension 69 to permit the piston 50 to be readily raised within or completely out of the upper tubular section 42 of the fluid chamber housing 40.

The permeameter-porosimeter assembly 10 may be installed on a commercially available universal test machine or on a press P (See FIG. 9) with calibrated force and displacement controls. The press P is engaged to the top 70 of the upper shaft extension 69 in order to actuate the piston 50 and control precisely the amount of pressure to which the piston 50 is subjected.

As previously discussed, it is sometimes necessary for the test sample S to be under compression when tested. For other types of material, the testing should be done with no compression on the central portion of the sample S being tested. Referring to FIG. 1, testing of a disk-shaped sample S in a direction normal to the plane of the sample and the central portion of the sample S under compression will now be described.

The lower holley block 30 is adjusted by rotating within the support block 28 to a position such that the upper surface of the lower porous spacer 36 positioned thereon is slightly above the upper surface of the support block 28. The disk-shaped sample S having a diametrical size larger than the diameter of the porous spacer 36 is positioned on the support block 28 with its outer edge and adjacent peripheral portion resting thereon and its central portion positioned over and resting upon the porous spacer 36. With the disk-shaped test sample S so positioned, the fluid chamber housing 40 is engaged thereto with the radial flange 47 sliding into the cylindrical upper wall 16 of the base 12 and the lower surface of the radial flange 47 engaged to the outer periphery of the disk-shaped sample S. Prior to such positioning of the fluid chamber housing 40, the upper holley block 46 is adjusted by threadedly rotating it within the lower section 44 to a position such that the lower surface of the upper porous spacer 36 engaged thereto will be slightly below the lower surface of the radial flange 47.

The compression ring 60 is then threadedly engaged to the base 12 and rotated to firmly clamp the peripheral edge of the disk-shaped sample S between the upper surface of the support block 28 and the lower surface of the radial flange 47 of the fluid chamber housing. The torque arms 64 may be used to tighten the compression ring 60 sufficiently to prevent any test liquid from flowing radially out of such edge portion. If desired, an O-ring in the upwardly facing annular groove 35 of the support block 28 may be used to assist in preventing the testing fluid from flowing radially. However, tests have shown that it usually is not necessary to use an O-ring. The compression on the edge portion may be in the range of 2.0 MegaPascals (MPa).

The previously described positioning of the lower holley block 30 and upper holley block 46 and of the respective porous spacers 36 engaged thereto will cause such porous spacers to compress the central portion of the sample S clamped therebetween. The amount of compression of the central portion being tested could be in the range of zero to several MegaPascals.

With the disk-shaped sample S thus positioned and the piston 50 elevated, the ball valves 58 are opened to introduce the testing fluid through the two lengths of tubing 55 and 57 into the space below the lower face of the enlarged head of the piston 50. The heater 66 will bring and, along with the thermocouple, maintain the testing fluid in the upper tubular section 42 to the desired temperature for testing. Following closing of the valves 58, the piston 50 is then actuated downwardly either by a commercially available uniform test machine or by a press with calibrated force and displacement controls to force the liquid through the flow passages 48 of the upper holley block 46, through the upper porous spacer 36, through the disk-shaped sample S, through the lower porous spacer 36 and through the flow passages 31 of the lower holley block 30 to the outlet tube 26 for collection in a separate container. The porous spacers 36 streamline the fluid flow uniformly over the disk-shape test sample S. As previously mentioned, the mean pore size of the porous spacers 36 must be at least ten times larger that that of the sample S so that the effect of such porous spacers 36 on the fluid flow will be minimal as compared to the effect of the test samples on such fluid flow.

Only a portion of the permeant testing fluid is forced through the sample S. Following completion of the downward actuation of the piston, the valves 58 are then opened and continued downward movement of the piston 50 will force the permeant fluid remaining in the fluid chamber housing 40 back to the storage tank 11.

The spherical top 70 of the piston upper extension rod 69 assists in assuring the concentricity of the axes of the piston 50 and the universal test machine or press.

For applications in which it is not desirable to apply compression to the central portion of the disk-shaped sample S prior to causing the fluid to flow through such sample, the porous spacers may be omitted. In that case, the lower holley block 30 may be rotated to a position such that its upper surface is slightly lower than the upper surface of the support block 28. With such positioning, the test sample S does not touch the lower holley block 30 during the setting up of this test; however, the lower holley block 30 will support the sample S as it gives under fluid pressure flowing therethrough in the normal direction during the testing operation.

Figure 6:
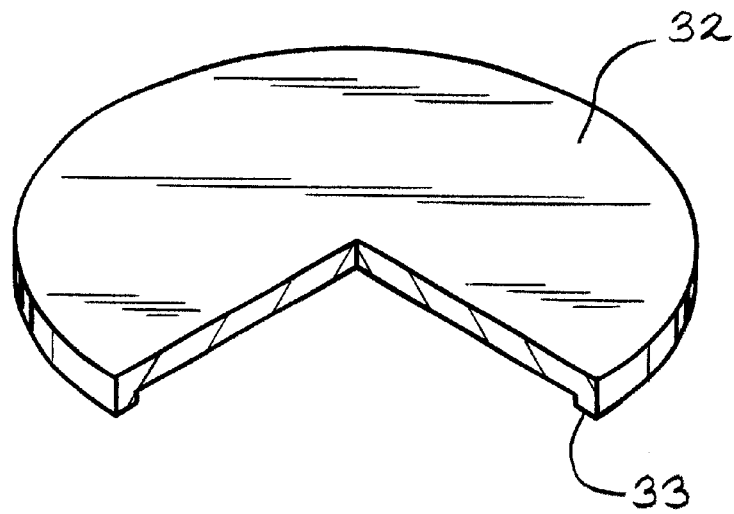
FIG. 6 is a perspective view of a plate member used with the embodiment of FIG. 5.
Figure 3:
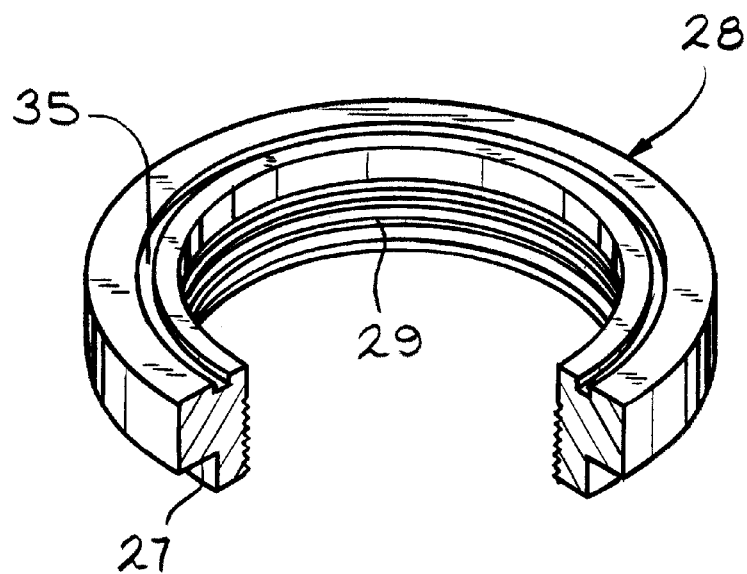
FIG. 3 is a perspective view of the support block of the assembly of FIG. 1.
Figure 4:
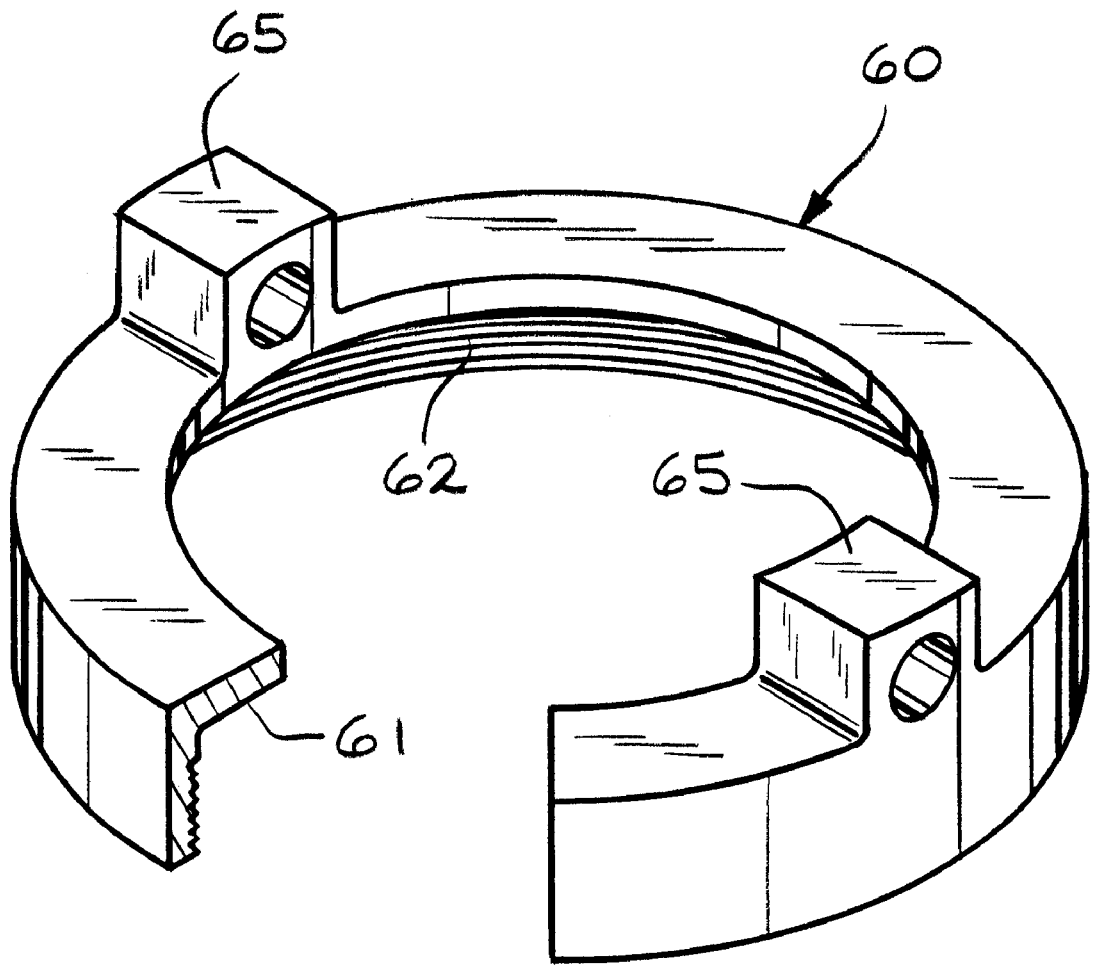
FIG. 4 is a perspective view of the compression member of the assembly of FIG. 1
Figure 5:
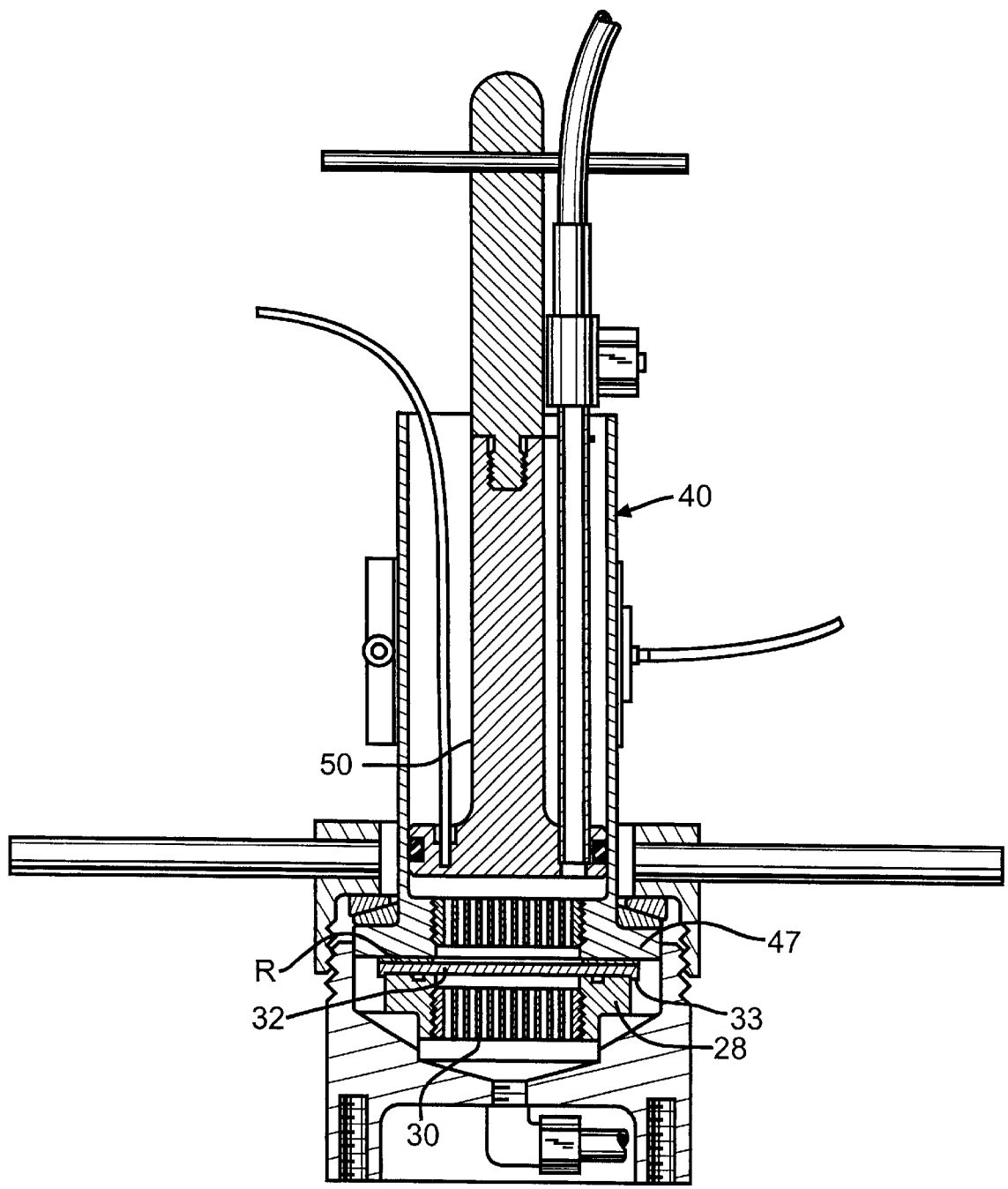
FIG. 5 is a perspective view of a modified embodiment for testing a ring-shaped sample in the lateral direction.

Referring to FIGS. 5 and 6, there is shown a modification to the assembly of FIG. 1 to permit lateral permeability testing of a ring-shaped sample R. As shown in FIG. 5, when the assembly 10 previously described is to be used to test a ring-shaped sample R in the lateral direction with the fluid flowing radially, a flat plate 32 will be positioned over the support block 28 to prevent liquid from flowing axially through the lower holley block 30. Preferably, the flat plate 32 has a downwardly extending flange 33 at its outer periphery which is sized to fit snuggly over the outer periphery of the support block 28. For conducting the lateral permeability test with this embodiment, the porous spacers described in the embodiment of FIGS. 1–4 are not used.

The ring-shaped sample R is positioned on the flat plate 32 in a position to be engaged by the lower surface of the radial flange 47 of the fluid chamber housing 40. In contrast to the previously described normal permeability test in which the outer periphery of the disk-shaped sample S was clamped between the radial flange and the upper surface of the support block 28 with sufficient pressure to prevent the test fluid from flowing radially therethrough, for the present lateral permeability test, the mechanical compression on the ring-shaped test sample R is on the order of 0.62 MPA, which amount of compression establishes a seal between the flat surfaces of the radial flange 47 and the support block 28, and the ring-shaped porous test sample R. As a result, the test fluid is caused to flow laterally outwardly through the ring-shaped test sample R. The amount of compression can be varied in order to measure permeability performance of the material from which the test sample R is formed under different amounts of compression.

Figure 7:
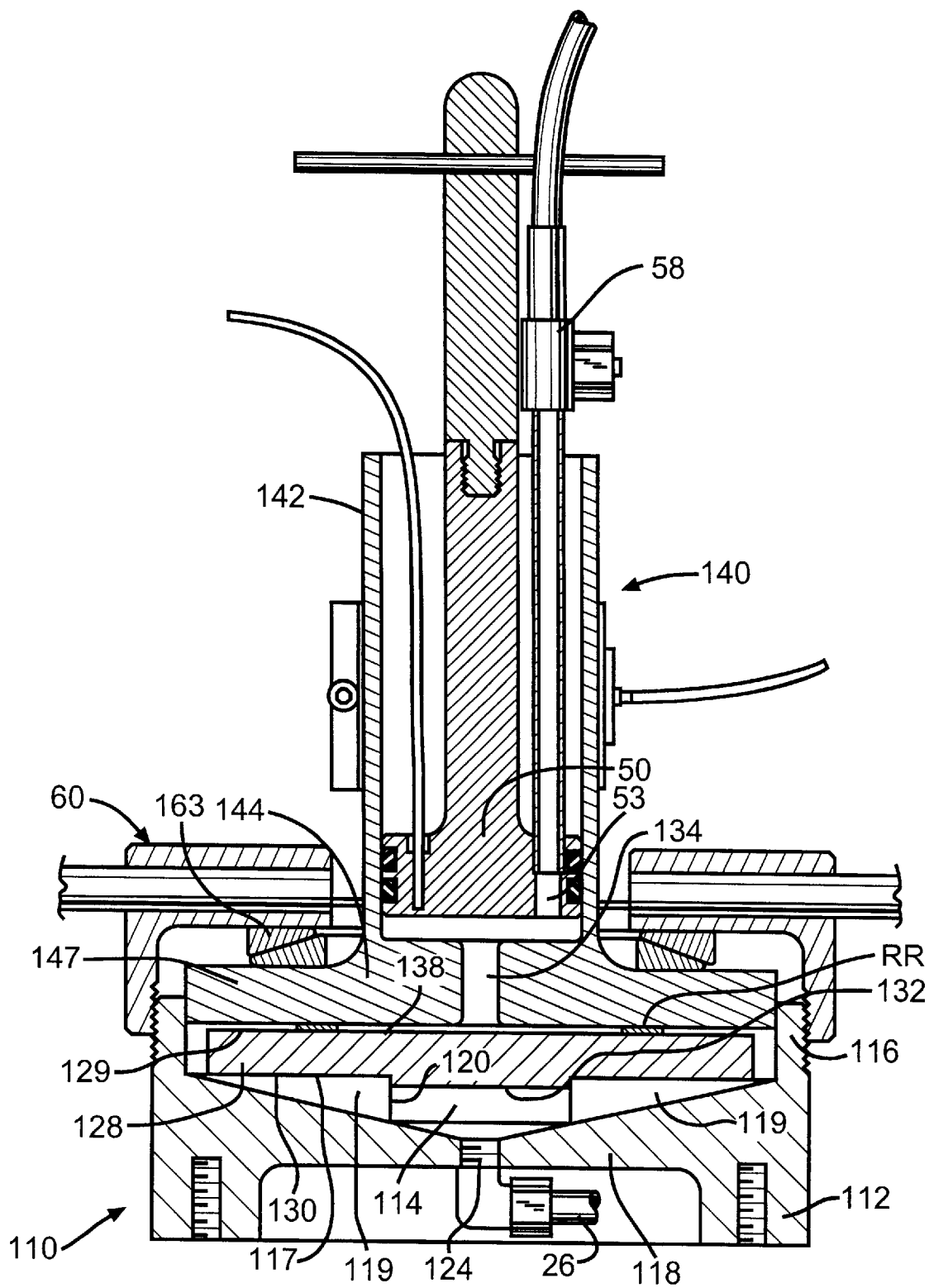
FIG. 7 is a view similar to FIG. 1 of another embodiment for testing a ring-shaped sample in the lateral direction.

Referring to FIG. 7, there is shown a modified permeameter-porosimeter assembly 110 which is suitable for taking measurements of a sample having a diameter larger than the maximum diameter of test sample tested on the assemblies described in FIG. 1–6. It also has the capability of taking measurements not only on a sample of the porous material itself, but also on a ring-shaped sample of porous material adhered to another member as part of an assembly such as a clutch friction plate.

The assembly 110 includes a base 112 similar to the base 12 of the embodiment of FIG. 1. Accordingly, the details of the base will not be described further except to note that the base 112 includes a shoulder 117 extending radially inwardly from a cylindrical sidewall 116 and that, there are provided a plurality of slots 119 in the shoulder to permit drainage of the permeant testing fluid. As in the previous embodiment, the transverse wall 118 has an opening 124 to which an outlet tube 26 may be affixed.

Positioned in the recess 114 is a support block 128 having a lower surface 130 resting upon the shoulder 117. As viewed from above, the support block 128 is disk-shaped having a flat circular upper surface 129. Extending downwardly from the lower surface 130 is a cylindrical projection 132 sized to fit within the cylindrical wall 120 extending downwardly from the shoulder 117 of the base 112. As can be seen from FIG. 7, in this embodiment there are no holley blocks and the solid disk-shaped upper surface 129 of the support block 128 prevents test fluid from flowing axially beyond such surface 129 until it has flowed radially outwardly through the ring-shaped sample RR being tested.

Engaged to the base 112 is a fluid chamber housing 140 having an upper axially extending tubular section 142 and an enlarged lower section 144. The lower section 144 has a radially outwardly extending flange 147 sized to fit within the cylindrical upper sidewall 116 of the base 112 in close engagement therewith. A piston 50 of the type described with respect to FIG. 1 is positioned in the upper tubular section 142 of the fluid chamber housing 140. The lower section 144 is provided with a passageway 134 extending axially therethrough to permit testing fluid to flow from the upper tubular section 142 following its introduction through aperture 53.

The compression ring 60 is engaged to the base 112 as described in the previous embodiment. Spherical washers 163 are positioned between the compression ring 60 and the upper surface of the radial flange 147.

In use, a ring-shaped test sample RR is positioned on the flat upper surface 129 of the support block 128. The fluid chamber housing 140 is then positioned on the base 112 with the outer edge of the radial flange 147 positioned in the cylindrical upper sidewall 116 of the base 112 and the lower surface of the lower section 144 engaged to the ring-shaped test sample RR. As can be seen in FIG. 7, such positioning of the fluid chamber housing 140 provides a gap 138 between the lower surface of the lower section 144 and the upper surface 129 of the support block 128. The amount of compression on the test sample RR is on the order of 0.62 MPA.

With the piston 50 in a raised position in the upper tubular section 142 of the fluid chamber housing 140, fluid is introduced through the aperture 53 of the piston 50 and flows through the axial passage 134 of the lower section 144 of the fluid chamber housing 140 and into the gap 138. Upon heating the test fluid to the desired temperature and closing the ball valve 58, the piston 50 is actuated downwardly to force the test fluid out of the fluid chamber housing 140, axial passage 134, radially through the gap 138 and radially through the ring-shaped test sample RR.

It is also possible to readily modify the embodiment of FIG. 7 to permit testing a disk-shaped sample in the normal direction. This may be accomplished by replacing the support block 128 having a solid upper surface 129 with a support block having a central aperture extending axially therethrough and placing a solid spacer ring between the disk sample and the fluid chamber as shown in FIG. 8.

Figure 8:
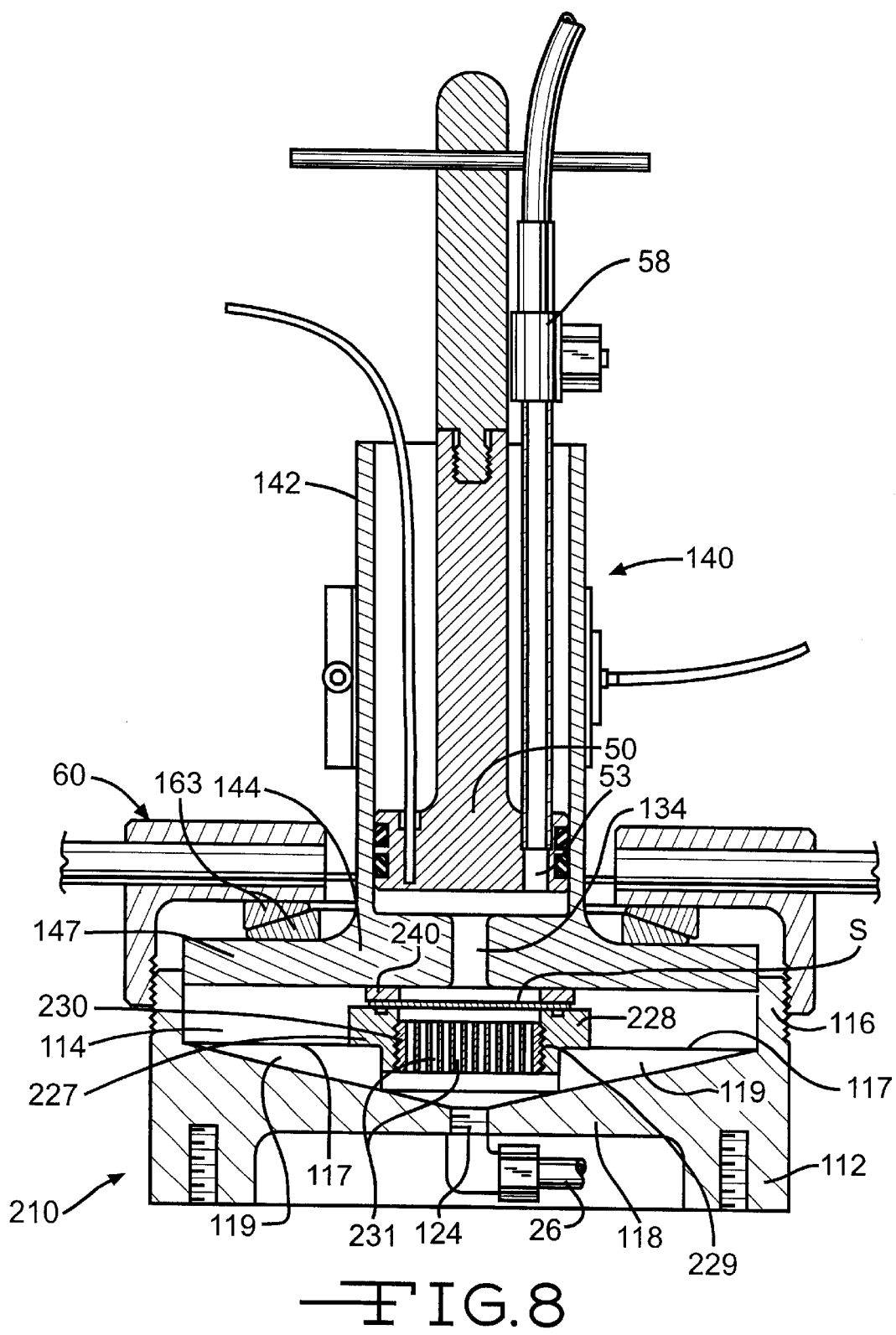
FIG. 8 is a view similar to FIG. 1 showing a further embodiment for testing a disk-shaped sample in the normal direction.
Figure 9:
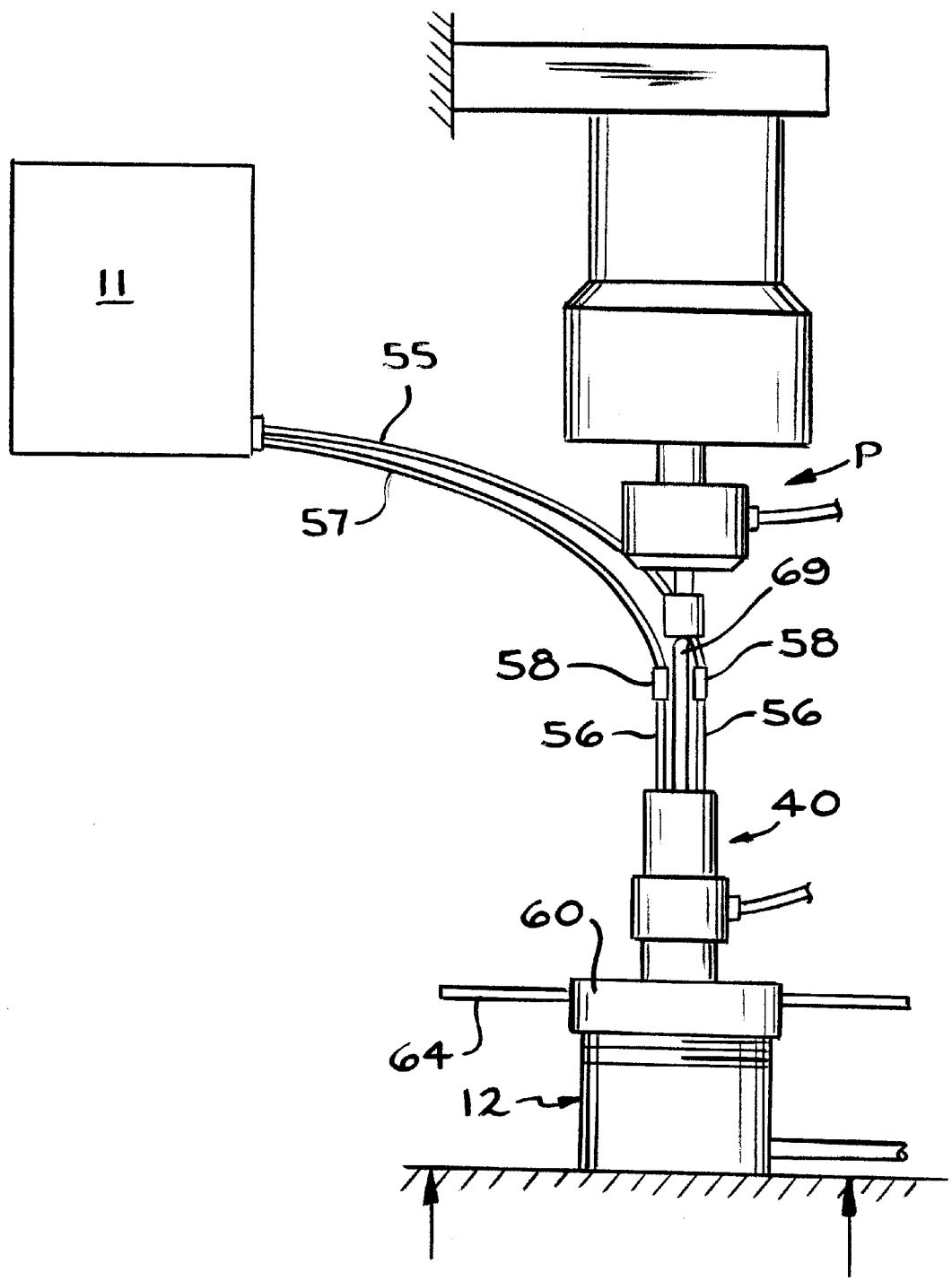
FIG. 9 is a schematic view showing a closed loop system for delivering permeant fluid to the permeameter-porosimeter assembly.

Referring to FIG. 8, there is shown a modified permeameter-porosimeter assembly 210 which is suitable for taking measurements of a disk-shaped sample S in the normal direction.

The assembly 210 includes a base 112 identical to the base of the embodiment of FIG. 7. Accordingly, the details of the base 112 will not be described further except to note that the transverse wall 118 has an opening 124 to which an outlet tube 26 may be affixed.

Positioned in the recess 114 is a ring-shaped support block 228 having an internal thread 229 and a radially outwardly extending flange 227 resting upon the shoulder 117 of the base 112.

The support block 228 houses a holley block 230 which is threadedly engaged to the internal thread 229. The holley block 230 is adjustable on the support block 228 by rotation when in threaded engagement with the support block 228 in order to position its upper end at the desired elevation. The holley block 230 is provided with a plurality of flow passages 231 extending axially therethrough. The number of flow passages 231 extending through the holley block 230 is such as to occupy substantially the entire transverse area of the holley block 230 giving an appearance of a honeycomb when viewed from an axial direction. The number of flow passages 231 coupled with the sizes thereof is such as to have minimal effect on the flow of the permeant flowing therethrough in relation to permeant flowing through the sample S being tested. If desired, a porous spacer may be positioned on the holley block 230.

Engaged to the base 112 is a fluid chamber housing 140 which is identical to the fluid chamber housing 140 of the embodiment of FIG. 7. A piston 50 of the type described with respect to FIG. 1 is positioned in the upper tubular section 142 of the fluid chamber housing 140. The lower section 144 is provided with a passageway 134 extending axially therethrough to permit permeant to flow from the upper tubular section 142 following its introduction through aperture 53.

The compression ring 60 is engaged to the base 112 as described in the previous embodiments. Spherical washers 163 are positioned between the compression ring 60 and the upper surface of the radial flange 147.

In testing the sample S, after the sample S is positioned such that its peripheral edge rests upon the upper surface of the support block 228 with its central portion to be tested positioned over the holley block 230, an annular solid spacer ring 240 having a thickness in the range of 5 mm±2 mm is positioned over such peripheral edge of the sample S. The fluid chamber housing 140 is then positioned in the base 112 with the lower section 144 engaging the spacer ring 240. Engagement of the compression ring 60 to the base 112 as previously described will cause the spacer ring 240 to compress the peripheral edge of the sample S against the upper surface of the support block 228 with sufficient compressive force to prevent permeant from flowing radially outwardly. If desired, an annular seal may be placed in the annular groove in the upper surface of the support block. The permeant may then be introduced through the aperture 53 of the piston 50, the passageway 134, through the sample S, in a normal direction thereto, through the flow passages 231 and out of the outlet 124 as previously described.

By measuring the pressure at which the test fluid is forced through the sample S, R, or RR, the thickness of the sample S or lateral breadth through which the test fluid flows for samples R and RR, weight of such samples, the compressive load on the portions of the samples being tested and flow time, it is possible to calculate permeability, porosity, pore size distribution, average pore size and number of pores per unit area.

A major feature of the permeameter of the present invention is its ability to determine the liquid permeability of friction materials used in wet clutch applications in automatic transmissions. A wet clutch contains a number of inner (or outer) splined friction plates and outer (or inner) splined separator plates which are packed alternatingly between a hub and a housing. The inner spline plates are attached to the hub and the outer splined plates are attached to the housing. The friction plates are made of porous friction materials which are bonded on steel core plates for mechanical support. Ordinarily, the friction plates and the separator plates rotate at different speeds before the clutch is engaged. Oil flow is supplied to the clearance between the plates through the radial holes on the hub for cooling and lubrication purposes. During a clutch engagement, a piston compresses the plates. The oil in between the plates is squeezed out of interface or permeates into and out of pores of friction material. At the beginning of an engagement, the oil permeates into friction material in the normal directions and permeates out of material in the lateral direction. At the end of an engagement, the oil may be squeezed in or out of pores depending on the direction of acceleration and the rate of compression. The engagement is completed when there is no speed differential between the friction plates and the separator plates. The torque capacity of a clutch depends on the thermal and the mechanical durability of the friction material and the coefficient of friction of the interface.

Permeability affects the interface temperature and, hence, the thermal durability of a friction material. Furthermore, permeability affects the shape of torque response curve by raising or lowering the initial coefficient of friction at the beginning of an engagement. A decreasing coefficient of friction with decreasing speed defines a positive torque curve shape and the increasing coefficient of friction with decreasing speed means a negative torque curve shape. Since a negative torque curve shape has the preconditions for stick-slip and shudder, a positive torque curve shape is desirable.

Friction material experts want to measure and control the permeability in normal and planar directions so that they can investigate the relations between the permeability of a friction material and the material's wet friction performance. The clutch thermal models and the clutch engagement models require accurate measurements of permeability constants to predict the performance of friction materials.

In addition to providing data for the mathematical models, the new permeameter also allows investigation of interactions of automatic transmission fluids with friction materials. Two transmission fluids having the same viscosity at the test temperature may exhibit different permeation behavior due to the differences in their additive content and chemistry. In addition to the permeability, the porosity can be calculated from the measurements taken with the new permeameter. Porosity affects the mechanical strength and the coefficient of friction of a friction material.

EXAMPLE I

The normal permeability test was performed on a sample which was a disk having a diameter of 63 mm. The outer rim of sample from 50.8 mm to 63 mm was compressed in between the flat upper surface of the support block 28 and lower surface of the lower section 44 of the fluid chamber housing 40 to prevent side leakage. The pressure on the outer rim of the sample was 2 MPa. The test fluid was caused to flow through the 50.8 mm diameter center portion of the disk, having an area of 2027 mm$^2$. The test fluid was automatic transmission fluid, FN1996, with an absolute viscosity of $61.6 \times 10^{-3}$ (Pas) at room temperature (22.5° C.) and was caused to flow through the thickness of the sample, namely one (1) mm, at a fluid pressure of 0.23 MPa. The amount of fluid flowing through the sample was 292 cm$^3$.

EXAMPLE II

The lateral permeability test was performed on a ring-shaped sample of 63 mm ID and 82 mm OD. Therefore, the area of sample through which the fluid flowed was 227 mm$^2$. The distance the fluid flowed through the sample was 9.5 mm, i.e. the width of annulus of the ring. The test fluid was water, absolute viscosity of $1 \times 10^{-3}$ Pas and was flowed through the sample at a fluid pressure of 0.23 MPa. The mechanical compression of the sample was 0.62 MPa. The amount of fluid flowing through the sample was 292 cm$^3$.

The fluid flow rate was calculated from the measurements of fluid displacement and time. The volume of retained fluid was calculated from the measurements of weight and thickness of each sample before and after a test. The calculations previously described resulted in the permeability-porosity data.

It will be apparent to those skilled in the art that numerous changes and modifications can be made without departing from the scope of the invention. Accordingly, the scope of the invention should be determined solely by the scope of the appended claims.

I claim:

1. Apparatus for measuring flow of fluid through samples of porous material in either of a lateral or normal direction, said porous material samples having a peripheral edge and first and second spaced apart surfaces extending inwardly therefrom comprising:
    (a) a support member having a surface, said surface including an annular portion for supporting a sample so as to accomodate fluid flow in a normal direction thru such sample;
    (b) a fluid chamber housing including a cylindrical wall and an end wall cooperating to define a chamber for receiving fluid, said end wall having an annular surface cooperating with said support member annular surface to clamp annular portions of a sample first and second spaced apart surfaces adjacent said peripheral edge therebetween so as to accommodate radially outward or lateral fluid flow thru such sample;
    (c) an opening in said end wall for introducing fluid to said sample; and
    (d) a fluid flow controller for forcing said fluid under pressure through said opening and said sample.

2. The apparatus of claim 1 wherein said fluid flow controller includes a piston having a stem and an enlarged head, said enlarged head having an aperture permitting the introduction of fluid to said chamber and said opening, movement of said piston toward said sample controlling the flow of fluid through said sample.

3. The apparatus of claim 2 wherein said support member includes an opening and a holley block positioned in said opening, said holley block having a plurality of passageways extending therethrough to receive fluid passing through said sample.

4. Apparatus for measuring flow of fluid through porous material comprising:
    (a) a support member having (1) an annular surface defining an opening for supporting a discrete sample of said material and (2) a holley block positioned in said opening, said holley block having a plurality of passageways extending therethrough to receive fluid passing through said sample, said holley block being threadedly retained in said support member opening and rotatable to vary the position of said holley block relative to said support member surfacer;
    (b) a fluid chamber housing including a cylindrical wall and an end wall cooperating to define a chamber for receiving fluid, said end wall having a surface cooperating with said support member surface to clamp said sample therebetween;
    (c) an opening in said end wall for introducing fluid to said sample; and
    (d) a fluid flow controller for forcing said fluid under pressure through said opening and said sample, said fluid flow controller including a piston having a stem and an enlarged head, said enlarged head having an aperture permitting the introduction of fluid to said chamber and said opening.

5. Apparatus for measuring flow of fluid through porous material comprising:
    (a) a support member having (1) an annular surface defining an opening for supporting a discrete sample of said material and (2) a holley block positioned in said opening, said holley block having a plurality of passageways extending therethrough to receive fluid passing through said sample, said holley block being threadedly retained in said support member opening and rotatable to vary the position of said holley block relative to said support member surface;

(b) a fluid chamber housing including a cylindrical wall and an end wall cooperating to define a chamber for receiving fluid, said end wall having a surface cooperating with said support member surface to clamp said sample therebetween;

(c) an opening in said end wall for introducing fluid to said sample; and (d) a fluid flow controller for forcing said fluid under pressure through said opening and said sample, said fluid flow controller including a piston having a stem and an enlarged head, said enlarged head having an aperture permitting the introduction of fluid to said chamber and said opening; and (e) a porous spacer on said holley block in a position to be engaged by said sample, said porous spacer permitting the flow of fluid therethrough.

6. The apparatus of claim 3 further including a second holley block positioned in the opening of said fluid chamber housing end wall, said second holley block having a plurality of passageways extending therethrough to receive fluid passing through said piston enlarged head aperture.

7. The apparatus of claim 1 wherein said support member includes an opening and a holley block positioned in said opening, said holley block having a plurality of passageways extending therethrough to receive fluid passing through said sample.

8. The apparatus of claim 7 further including an annular spacer ring overlying an annular portion adjacent said peripheral edge of a sample supported on said support member, said spacer ring engaged by said fluid chamber housing end wall and encircling said end wall opening.

9. The apparatus of claim 1, wherein said support member has a solid surface cooperating with said end wall surface to clamp said sample therebetween, said solid surface causing fluid flowing through said sample to flow radially outwardly.

10. The apparatus of claim 1 wherein said support member includes an opening and further including a plate member having a solid surface, said plate member engaged to said support member overlying said opening and causing fluid flowing through said sample to flow radially outwardly.

11. The apparatus of claim 1 wherein said fluid chamber housing includes an outwardly extending flange and further including (i) a base member, said support member being retained in said base member and (ii) a clamping member engageable with said base member, said clamping member operable to retain said outwardly extending flange to said support member.

12. Apparatus for measuring flow of fluid through porous material comprising:

(a) a support member having an annular surface for supporting a discrete sample of said material, said sample including a peripheral edge and first and second spaced apart surfaces extending inwardly therefrom;

(b) a fluid chamber housing including a cylindrical wall and an end wall cooperating to define a chamber for receiving fluid, said end wall having an annular surface cooperating with said support member annular surface to clamp annular portions of said sample first and second spaced apart surfaces adjacent said peripheral edge therebetween;

(c) an opening in said end wall for introducing fluid to said sample;

(d) a fluid flow controller for forcing said fluid under pressure through said opening and said sample;

(e) a base member, said support member being retained in said base member;

(f) a clamping member engageable with said base member, said clamping member operable to retain said outwardly extending flange to said support member; and (g) a set of self-aligning spherical washers between said clamping member and said flange to provide uniform pressure over a sample of said material.

13. The apparatus of claim 1 wherein said fluid chamber housing includes an outwardly extending flange and further including a base member having threads and a compression member threadedly engaged to said base member, said compression member operable to place pressure upon said outwardly extending flange to retain said fluid chamber housing to said support member and to compress a test sample.

14. The apparatus of claim 13 wherein said fluid flow controller includes a piston having a stem and an enlarged head, said enlarged head having an aperture permitting the introduction of fluid to said chamber and said opening.

15. The apparatus of claim 14 wherein said support member includes an opening and a holley block positioned in said opening, said holley block having a plurality of passageways extending therethrough to receive fluid passing through said sample.

16. The apparatus of claim 15 further including a porous spacer on said holley block in a position to be engaged by said sample, said porous spacer permitting the flow of fluid therethrough.

17. The apparatus of claim 15 wherein said holley block is threadedly retained in said opening and may be rotated to vary the position of said holley block relative to said supporting surface.

18. The apparatus of claim 15 further including a second holley block positioned in the opening of said fluid chamber housing end wall, said second holley block having a plurality of passageways extending therethrough.

19. The apparatus of claim 1 further including a heater and temperature controller for controlling the temperature of said fluid in said fluid chamber housing.

20. The apparatus of claim 1 further including a fluid storage tank and closed loop fluid transportation line.

21. A method for measuring a sample of porous material for both normal and lateral permeability, said sample having spaced apart first and second sides comprising the steps of:

(a) removing a disk shaped member from said sample thereby leaving a second portion of said sample, said disk shaped member defining a first sub-sample having an annular outer edge extending between said first and second sides and said second portion defining a second sub-sample having an aperture defined by an annular inner edge extending between said first and second sides;

(b) clamping an annular portion of said first sub-sample adjacent said annular outer edge between first and second annular support members and flowing permeant fluid in a normal direction through said first sub-sample; and (c) clamping an annular portion of said second sub-sample adjacent said annular inner edge between first and second annular support members and flowing permeant fluid laterally through said second sub-sample outwardly from said annular inner edge.

* * * * *